United States Patent
Belfort et al.

(10) Patent No.: US 11,154,819 B2
(45) Date of Patent: Oct. 26, 2021

(54) ANTI-FOULING CHIRAL SURFACES FOR MEMBRANE FILTRATION AND METHODS THEREFOR

(71) Applicant: RENSSELAER POLYTECHNIC INSTITUTE, Troy, NY (US)

(72) Inventors: Georges Belfort, Slingerlands, NY (US); Joseph Imbrogno, Massapequa, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 16/690,481

(22) Filed: Nov. 21, 2019

(65) Prior Publication Data
US 2020/0197874 A1 Jun. 25, 2020

Related U.S. Application Data

(63) Continuation of application No. 15/324,372, filed as application No. PCT/US2015/039538 on Jul. 8, 2015, now Pat. No. 10,532,326.
(Continued)

(51) Int. Cl.
*B01D 65/08* (2006.01)
*B01D 67/00* (2006.01)
(Continued)

(52) U.S. Cl.
CPC .......... *B01D 65/08* (2013.01); *B01D 61/007* (2013.01); *B01D 67/0093* (2013.01);
(Continued)

(58) Field of Classification Search
CPC .. B01D 61/007; B01D 67/0093; B01D 71/68; B01D 71/72
See application file for complete search history.

(56) References Cited

U.S. PATENT DOCUMENTS

| | | | | |
|---|---|---|---|---|
| 2010/0035074 A1* | 2/2010 | Cohen | ............... | B05D 3/144 |
| | | | | 428/500 |
| 2012/0226054 A1* | 9/2012 | Miller | ............... | B01J 20/28078 |
| | | | | 549/286 |
| 2013/0267801 A1* | 10/2013 | Romey | ............... | A61B 5/1459 |
| | | | | 600/316 |

OTHER PUBLICATIONS

Ingole et al., "Membrane separation processes: Optical resolution of lysine and asparagines amino acids," Desalination, vol. 343, Jun. 16, 2014, pp. 75-81; Available online Oct. 25, 2013; http://dx.doi.0rg/IO.IOI6/j. lesal.2013.10.009, (2013). (Year: 2013).*
(Continued)

*Primary Examiner* — Bradley R Spies
(74) *Attorney, Agent, or Firm* — Murtha Cullina LLP; Anthony P. Gangemi

(57) ABSTRACT

The present disclosure relates to, inter alia, a modified surface comprising an optically active monomer, a polymeric material having a surface onto which the optically active monomer is covalently bound. In one aspect, a membrane comprising an optically active monomer, a poly (aryl sulfone) membrane having a surface onto which the optically active monomer is covalently bound. The present disclosure also relates to a method of modifying a surface, the method comprising applying sufficient energy to a surface to induce covalent bonding with an optically active monomer, and contacting the optically active monomer with the surface. In one aspect, a method of modifying a surface of a poly(aryl sulfone) membrane is disclosed. In another aspect, a method of synthesizing an optically active monomer is disclosed. In one aspect, a method of filtration of chiral compounds is disclosed.

19 Claims, 5 Drawing Sheets

Related U.S. Application Data

(60) Provisional application No. 62/022,430, filed on Jul. 9, 2014.

(51) Int. Cl.
    *B01D 71/68*     (2006.01)
    *B01D 71/82*     (2006.01)
    *C07D 207/416*     (2006.01)
    *B01D 61/00*     (2006.01)
    *B01D 69/02*     (2006.01)

(52) U.S. Cl.
    CPC ............ *B01D 69/02* (2013.01); *B01D 71/68* (2013.01); *B01D 71/82* (2013.01); *C07D 207/416* (2013.01)

(56) References Cited

OTHER PUBLICATIONS

Zhou et al., "Asymmetric Anionic Polymerization of Chiral (R)-(+)-N-a-Methylbenzylmaleimide with Chiral Ligand/ Drganometal Complex," Polymer Journal, 32(7):552-559 (2000). (Year: 2000).*

Oishi et al., "Asymmetric Polymerization of N-ortho-or para-Substituted Phenylmaleimide Using Chiral Anionic nitiators," Polymer Journal, 35(3):245-254 (2003). (Year: 2003).*

Gumi, Tania etal—"Separation of propranolol enantiomers through membranes based on chiral derivatized polysulfone"—Polymer 46 (2005) 12306-12312 (Year: 2005).*

Lin, Aiguo et al—Preparatin and characterization of a new negatively charged polytetrafluoroethylene membrane for treating oilfield wastewater—Journal of Membrane Science 371 (2011) 286-292 (Year: 2011).*

* cited by examiner

ANTI-FOULING CHIRAL SURFACES FOR MEMBRANE FILTRATION AND METHODS THEREFOR

CROSS-REFERENCE TO RELATED APPLICATION

This application is a continuation of U.S. Utility patent application Ser. No. 15/324,372, filed Jan. 6, 2017, which is a national stage filing of International Application No. PCT/US2015/039538, filed on Jul. 8, 2015, which claims the benefit of U.S. Provisional Patent Application Ser. No. 62/022,430, filed Jul. 9, 2014, the disclosures of which are hereby incorporated by reference herein in their entireties.

STATEMENT REGARDING FEDERALLY SPONSORED RESEARCH AND DEVELOPMENT

This invention was made with U.S. Government support under Grant Number DOE-DE-FG02-09ER 16005 awarded by U.S. Department of Energy. The United States Government has certain rights in the invention.

FIELD OF THE INVENTION

The present invention generally relates to anti-fouling chiral surfaces for membrane filtration, and protein resistance, and to processes for the modification of surfaces for protein resistance by adding optically active monomers to surfaces.

BACKGROUND OF THE INVENTION

Biological fouling is a major limitation in many applications, including food and biotechnology processing, marine structures such as ship hulls and oil rigs, surgical instruments, and wastewater treatment Biological fouling (adhesion of interacting retained solutes like proteins, viruses, DNA, and cells) and concentration polarization (build-up of iron-interacting retained solutes like tons near the surface) ultimately lead to a decrease in performance and an increase in energy use.

Ultrafiltration membranes are widely used in the biotechnology, food, beverage, and water industries. A major source of fouling is non-specific protein binding to the membrane surface. As upstream feed titers increase, especially in the biotechnology industry, the majority of the operating costs of the entire process are shifted heavily to the downstream processes.

For over 40 years, both interfacial polymerization and phase inversion have been the predominant methods for preparing asymmetric and composite polymeric membrane structures. Although these synthesis methods have been very successful, they are relatively complex, sensitive to small changes in the casting conditions, susceptible to residual chlorine, and produce rough membrane surfaces that enhance membrane fouling. Many research groups have sought novel synthesis methods for producing improved polymeric synthetic membranes without much success. Such membranes have too low a porosity (track etched), are too expensive (ceramic or stainless steel), possess too wide a pore size distribution (stretched PTFE), or too fragile (biological).

Thus, new high performance low-fouling synthetic membranes are needed. A facile, fast, and inexpensive method to assist in the discovery of new low fouling coatings is also urgently needed.

SUMMARY OF THE INVENTION

Briefly, the present invention satisfies the need for high performance low-fouling synthetic membranes for filtration. The present invention may address one or more of the problems and deficiencies of the art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

One aspect of the present disclosure relates to a modified surface comprising an optically active monomer and a polymeric material having a surface onto which the optically active monomer is covalently bound.

One aspect of the present disclosure relates to a membrane comprising an optically active monomer, and a poly (aryl sulfone) membrane having a surface onto which the optically active monomer is covalently bound.

In one aspect, the present disclosure provides a method of modifying a surface, the method comprising applying sufficient energy to a surface to induce covalent bonding with an optically active monomer, and contacting the optically active monomer with the surface.

In another aspect, the present disclosure provides a method of modifying a surface, the method comprising contacting an initiating agent to a surface onto which an optically active monomer is to be covalently bound, applying sufficient energy to the surface to induce covalent bonding with the optically active monomer, and contacting the optically active monomer with the surface.

In one aspect, the present disclosure provides a method of modifying a surface of a poly(aryl sulfone) membrane, the method comprising providing a poly(aryl sulfone) membrane having a surface, exposing the surface of the poly(aryl sulfone) membrane to an atmospheric pressure plasma (APP) source, contacting an optically active monomer with the surface of the poly(aryl sulfone) membrane, and applying heat to the surface of the poly(aryl sulfone) membrane.

In another aspect, the present disclosure provides a method of modifying a surface of a poly(aryl sulfone) membrane, the method comprising providing a poly(aryl sulfone) membrane having a surface, contacting an initiating agent with the surface of the poly(aryl sulfone) membrane, exposing the surface of the poly(aryl sulfone) membrane to an atmospheric pressure plasma (APP) source, contacting an optically active monomer with the surface of the poly(aryl sulfone) membrane, and applying heat to the surface of the poly(aryl sulfone) membrane.

One aspect of the present disclosure provides a method of synthesizing an optically active monomer comprising:
providing a solution comprising bis(2-methacryloyl)oxyethyl disulfide, wherein the bis(2-methacryloyl)oxyethyl disulfide has been contacted with a tris 2-carboxyethyl)phosphine (TCEP) reducing gel;
providing a solution comprising an optically active maleimide;
mixing the disulfide and maleimide solutions;
centrifuging the mixed solution; and
removing the TCEP reducing gel.

One aspect of the present disclosure is a method for filtration of chiral compounds, the method comprising:

providing a membrane in accordance with present disclosure; and passing a solution comprising chiral compounds through the membrane.

These and other objects, features, and advantages of this invention will become apparent from the following detailed description of the various aspects of the invention taken in conjunction with the appended claims and the accompanying drawings.

BRIEF DESCRIPTION OF THE DRAWINGS

The present invention will hereinafter be described in conjunction with the following figures, wherein.

DETAILED DESCRIPTION OF THE INVENTION

Figure 1:
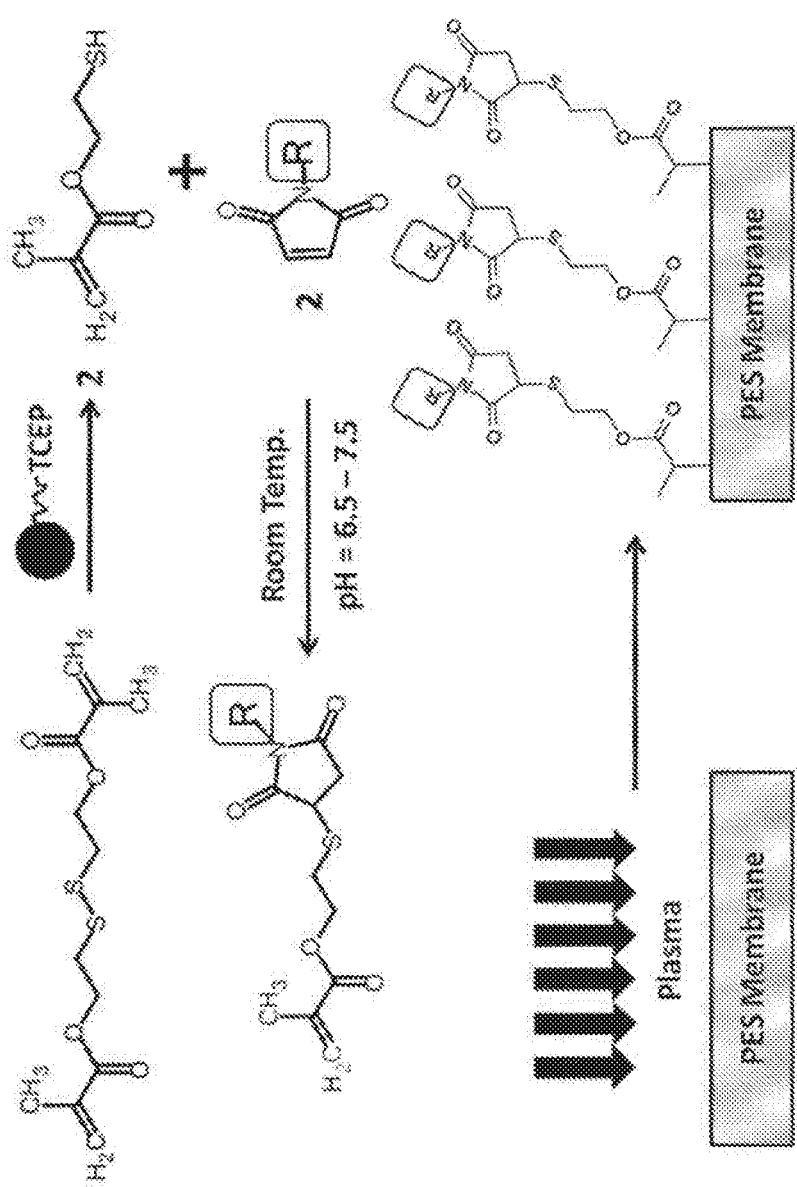
FIG. 1 depicts a reaction scheme showing monomers grafted onto polyether sulfone) membranes.

Aspects of the present invention and certain features, advantages, and details thereof, are explained more fully below with reference to non-limiting embodiments of the invention. Descriptions of well-known materials, fabrication tools, processing techniques, etc. are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure, and such embodiments fall within the scope of the invention as defined by the claims that follow.

The present disclosure relates to, inter alia, a modified surface comprising an optically active monomer covalently bound onto a surface, a membrane comprising an optically active monomer covalently bound to a surface of a poly(aryl sulfone) membrane, methods of modifying a surface, methods of modifying a surface of a poly(aryl sulfone) membrane, a method of synthesizing an optically active monomer, and a method of filtering chiral compounds.

In general the terms and phrases used herein have their art-recognized meaning, which can be found by reference to standard texts, journal references and contexts known to those skilled in the an. The following definitions are provided to clarify their specific use in the context of the invention.

As used herein, the term "chiral" refers to molecules which have the property of being non-superposable on their mirror image partner. "Enantiomers" are a pair of stereoisomers that are non-superposable mirror images of each other.

As used herein, the term "optically active" generally refers to presence of excess of one enantiomer over the other, and is not an indication that the monomer is pure enantiomer.

As used herein, the term "grafted onto" or "grafting" generally refer to addition of monomers onto a surface. The monomers form covalent bonds with the material forming the surface. For example, the covalent bonds are formed via free-radical polymerization, which occurs across the vinyl group of the methacrylate end of the monomer. Non-limiting examples of optimal solvent include organic solvent miscible with water, for example, acetone, deionized water, dimethylformamide (DMF), and alcohols, for example, ethanol and propanol.

One aspect of the present disclosure relates to a modified surface comprising an optically active monomer and a polymeric material having a surface onto which the optically active monomer is covalently bound.

In certain embodiments, the optically active monomer provides a repeating unit of the following Formula I:

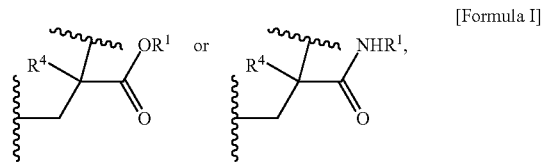

[Formula I]

wherein $R^1$ is a maleimide derivative in which $R^1$ contains at least one chiral center, and $R^4$ is H or $CH_3$.

In certain embodiments, the optically active monomer provides a repeating unit of the following Formula II:

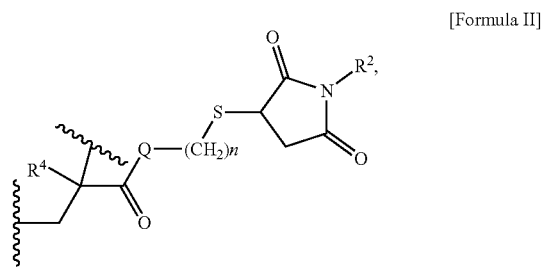

[Formula II]

wherein $R^2$ is an optically active substituent,
n is a number from 1 to 6,
Q is NH or O, and
$R^4$ is H or $CH_3$.

In certain embodiments, $R^2$ is

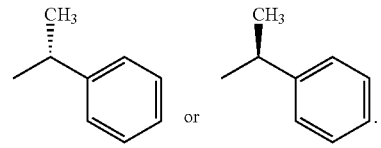

One aspect of the present disclosure relates to a membrane comprising an optically active monomer, and a poly (aryl sulfone) membrane having a surface onto which the optically active monomer is covalently bound.

In some embodiments, the poly(aryl sulfone) membrane is a poly(ether sulfone) membrane. Commercially available poly(ether sulfone) membranes generally have a wide Molecular Weight Cut Off (MWCO) range, for example, between 1 kDa to 1,000,000 kDa. In some embodiments, the MWCO range for poly(ether sulfone) membrane may be from 10 kDa to 300 kDa. In a particular embodiment, the poly(ether sulfone) membrane is a 100 k Da MWCO poly(ether sulfone) membrane.

In certain embodiments, the optically active monomer provides a repeating unit of the following Formula II:

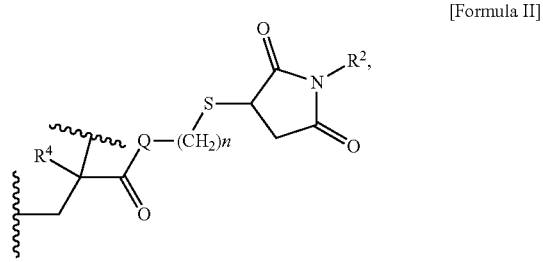

[Formula II]

wherein $R^2$ is an optically active substituent,
n is a number from 1 to 6,
Q is NH or O, and
$R^4$ is H or $CH_3$.

In certain embodiments, $R^2$ is

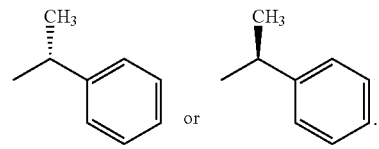

In certain embodiments, the optically active monomer provides a repeating unit of the following Formula III:

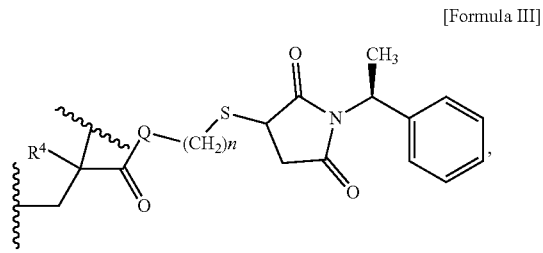

[Formula III]

wherein Q is NH or O,
n is a number from 1 to 6, and
$R^4$ is H or $CH_3$.

In certain embodiments, the optically active monomer provides a repeating unit of the following Formula IV:

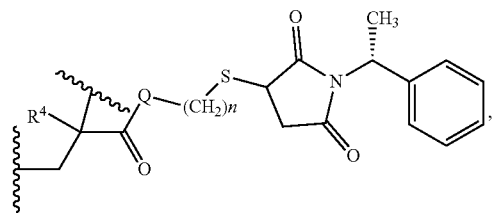

[Formula IV]

wherein Q is NH or O,
n is a number from 1 to 6, and
$R^4$ is H or $CH_3$.

In some embodiments, the optically active monomer is a vinyl ester linked to an optically active maleimide or a vinyl amide linked to an optically active maleimide, wherein the maleimide may be a (R)-(+)-N-(1-Phenylethyl)maleimide or a (S)-(+)-N-(1-Phenylethyl)maleimide.

Another aspect of the present disclosure relates to a method of modifying a surface, the method comprising applying sufficient energy to a surface to induce covalent bonding with an one optically active monomer, and contacting the optically active monomer with the surface.

In another aspect, the present disclosure provides a method of modifying a surface, the method comprising contacting an initiating agent to a surface onto which an optically active monomer is to be covalently bound, applying sufficient energy to the surface to induce covalent bonding with an optically active monomer, and contacting the optically active monomer with the surface.

In one aspect, the present disclosure provides a method of modifying a surface of a poly(aryl sulfone) membrane comprising:
  providing a poly(aryl sulfone) membrane having a surface;
  exposing the surface of the poly(aryl sulfone) membrane to an atmospheric pressure plasma (APP) source;
  contacting an optically active monomer with the exposed surface of the poly(aryl sulfone) membrane; and
  applying heat to the surface of the poly(aryl sulfone) membrane.

In another aspect, the present disclosure provides a method of modifying a surface of a poly(aryl sulfone) membrane, the method comprising:
  providing a poly(aryl sulfone) membrane having a surface;
  contacting an initiating agent with the surface of the poly(aryl sulfone) membrane;
  exposing the surface of the poly(aryl sulfone) membrane to an atmospheric pressure plasma (APP) source;
  contacting an optically active monomer with the surface of the poly(aryl sulfone) membrane; and
  applying heat to the surface of the poly(aryl sulfone) membrane.

U.S. Pat. No. 5,468,390, co-invented by one of the present co-inventors and which is incorporated herein by reference, discloses a photochemical grafting process that permits the attachment of free radically polymerizable monomers to the surface of poly(aryl sulfone) and poly(ether sulfone) membranes. This represents an alternative method of providing the energy necessary to initiate a reaction between a membrane and a monomer.

In certain embodiments of the method of modifying a surface of a poly(aryl sulfone) membrane, the step of applying heat is carried out by exposing a source of heat to the poly(aryl sulfone) membrane, wherein the surface has been exposed to an APP source and the surface has been contacted with an optically active monomer. As used herein, the "applying heat" refers to the process of subjecting the poly(aryl sulfone) membrane to a particular raised temperature.

In a particular embodiment, the poly(aryl sulfone) membrane is exposed to heat in the range from 30° C. to 100° C., preferably from 50° C. to 70° C.

In certain embodiments of the method of modifying a surface of a poly(aryl sulfone) membrane, the poly(aryl sulfone) membrane is exposed to heat for 1 to 4 hours.

In a particular embodiment of the method of modifying a surface of a poly(aryl sulfone) membrane, the heat is applied by placing the poly(aryl sulfone) membrane in an oven at a temperature between 50° C. to 70° C. for 1 to 4 hours.

In certain embodiments, the AFP source is helium and oxygen gases.

The modified surface and the membrane of the present disclosure may be light sensitive or non-light sensitive. For example, to modify a non-light sensitive surface, an initiating agent, for example, benzophenone, could be added to activate the surface for covalent grafting.

In certain embodiments, the method further comprises contacting the heated surface of the poly(aryl sulfone) membrane with water.

In certain embodiments of the method of modifying a surface of a poly(aryl sulfone) membrane, the optically active monomer is a compound of the following Formula I:

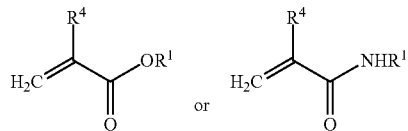

[Formula I]

wherein $R^1$ is a maleimide derivative in which $R^1$ contains at least one chiral center, and $R^4$ is H or $CH_3$.

In certain embodiments of the method of modifying a surface of a poly(aryl sulfone) membrane, the optically active monomer is a compound of the following Formula II:

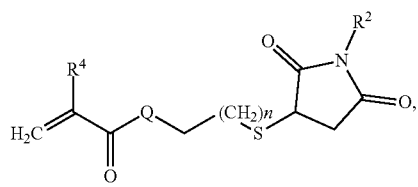

[Formula II]

wherein $R^2$ is an optically active substituent,
n is a number from 1 to 6,
Q is NH or O, and
$R^4$ is H or $CH_3$. The optically active monomer is covalently bound onto the surface of the poly(aryl sulfone) membrane.

In certain embodiments of the method of modifying a surface of a poly(aryl sulfone) membrane, $R^2$ is

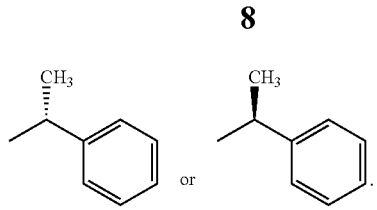

In certain embodiments of the method of modifying a surface of a poly(aryl sulfone) membrane, the optically active monomer is a compound of the following Formula III:

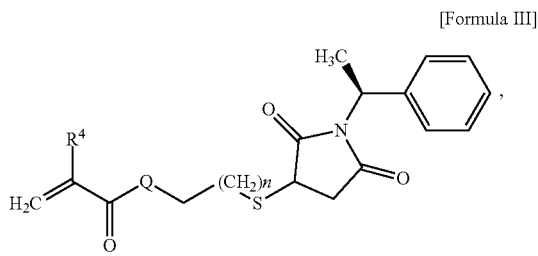

[Formula III]

wherein Q is NH or O,
n is a number from 1 to 6, and
$R^4$ is H or $CH_3$.

In certain embodiments of the method of modifying a surface of a poly(aryl sulfone) membrane, the optically active monomer is a compound of the following Formula IV:

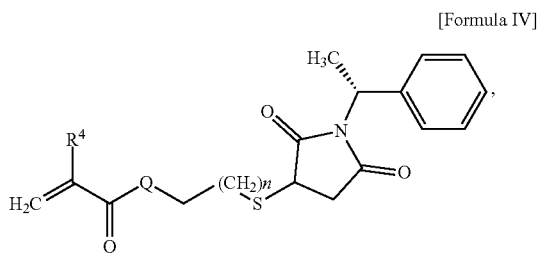

[Formula IV]

wherein Q is NH or O,
n is a number from 1 to 6, and
$R^4$ is H or $CH_3$.

In one aspect, the present disclosure provides a method of synthesizing an optically active monomer comprising:
  providing a solution comprising bis(2-methacryloyl)oxyethyl disulfide, wherein the bis(2-methacryloyl)oxyethyl disulfide has been contacted with a tris(2-carboxyethyl)phosphine (TCEP) reducing gel;
  providing a solution comprising a maleimide;
  mixing the disulfide and maleimide solutions;
  centrifuging the mixed solution; and
  removing the TCEP reducing gel.

In a particular embodiment of the method of synthesizing an optically active monomer, the maleimide is (R)-(+)-N-(1-Phenylethyl)maleimide.

In a particular embodiment of the method of synthesizing an optically active monomer, the maleimide is (S)-(+)-N-(1-Phenyleihyl)maleimide.

In certain embodiments of the method of synthesizing an optically active monomer, the organic solvent is miscible with water. The appropriate solvent will be apparent to one skilled in the arts in view of the present disclosure.

In a particular embodiment of the method of synthesizing an optically active monomer, the method further comprises sonicating the maleimide solution for 5 to 30 minutes, preferably for 5 to 15 minutes.

In a particular embodiment of the method of synthesizing an optically active monomer, the method further comprises mixing by rotating the bis(2-methacryloyl)oxyethyl disulfide solution for 1 to 60 minutes, preferably for 5 to 30 minutes.

In a particular embodiment of the method of synthesizing an optically active monomer, the method further comprises rotating the mixed solution for 12 to 28 hours, preferably for 18 to 26 hours, at a temperature between 20° C. to 25° C. For example, the mixed solutions may be continuously rotated or inverted.

In one aspect, the present disclosure provides a method for filtration of chiral compounds, the method comprising: providing a membrane in accordance with the present disclosure; and passing a solution comprising chiral compounds through the membrane.

In various aspects, the modified surface of the present disclosure is likely to be used at the bench scale and the industrial scale for filtering of small organic molecules from other small organic molecules, small organics from proteins, natural proteins from synthetic proteins of opposite chirality, etc. Having an additional parameter for separation during filtration processes where chirality is present is immensely powerful and novel.

The present disclosure can also be implemented into various industries and purposes, For example, chiral membranes could be used for various different applications separating different reagents based on chirality.

In another embodiment, the present disclosure could also have medical applications. For example, the membrane in accordance to the present disclosure could be used in dialysis to remove one stereoisomer from a patient.

Solutions comprising optically active monomers in accordance with the present disclosure could be applied to various other surfaces. For example, solutions comprising optically active monomers in accordance with the present disclosure could be used to coat ship hulls to reduce marine fouling. Another example, solutions comprising optically active monomers in accordance with the present disclosure could be used to graft onto surgical instruments, including for example, surgical tubing, to reduce the adhesion of proteins from the body. Solutions comprising optically active monomers in accordance with the present disclosure could also be applied onto walls to reduce the spread of infectious diseases in a setting such as a hospital.

Persons having ordinary skill in the art will readily recognize possible substitutions and modifications within the following schemes, that fail within the scope of the present invention, and that can be used to prepare non-illustrated embodiments of the inventive anti-fouling chiral surfaces and methods therefor.

EXAMPLES

The invention will now be illustrated, but not limited, by reference to the specific embodiments described in the following examples.

Materials

Bis(2-methacryloyl)oxyethyl disulfide (99%), (R)-(+)-N-(1-Phenylethyl)maleimide (97%), and (S)-(−)-N-(1-Phenylethyl)maleimide (97%) were purchased from Sigma Aldrich (St. Louis, Mo.) and were used without further purification. Immobilized TCEP Disulfide Reducing Gel was purchased from Thermo Scientific (Rockford, Ill.). Spin filter tubes and receiving tubes (2 mL) were obtained from Novagen (Darmstadt, Germany). 96-well filter plates (CMR #1746-3, Seahorse Labware. Chicopee, Mass.) were used for the HTP grafting and filtration. PES membranes (100 kDa MWCO) with an effective area of 19.95 mm$^2$ were mounted and heat-sealed by the manufacturer (Seahorse Bioscience, North Billerica, Mass.) on the bottom of each well of a 96-well filter plate (each well has a volume of 400 μL). The membranes were washed and soaked in DI water overnight before use to remove surfactant. Industrial grade helium and oxygen gases were used as a plasma source (Airgas, Albany, N.Y.). Solution for the static protein fouling assay was prepared by dissolving 1 mg/mL bovine serum albumin (BSA, molecular weight, (MW) ~67 kDa, pI 4.7) in phosphate buttered saline (PBS) solution. BSA and PBS tablets were purchased from Sigma Aldrich (St. Louis, Mo.). When dissolved in 200 mL of water, a PBS tablet yields 10 mM phosphate butter, 2.7 mM potassium chloride and 137 mM sodium chloride with pH 7.4 at 25° C.

Methods

Monomer Synthesis

Bis(2-methacryloyl)oxyethyl disulfide (0.1 mmol) was mixed with 500 μL TCEP reducing gel (4% cross-linked beaded agarose, supplied as a 50% slurry) in one container, while each of the maleimides (~0.2 mmol) were used in excess and mixed with 400-600 μL of an appropriate organic solvent that was miscible with water (Table 1). The separate maleimide containing tubes were then sonicated for 5 minutes and the disulfide containing tubes were rotated for 15 min. in order to allow for the pre-reduction of the disulfide reagent. The two solutions were then mixed and rotated overnight at 22° C. while the reaction proceeded. The new monomers are shown in Table 2. The reaction scheme is presented in FIG. 1. The crude mixture was then added to a spin filter and receiver tube and centrifuged at 2500 rpm for 1 min. The crude product was analyzed using mass spectrometry (MS). A maleimide with just a hydrogen as an R group was not studied due to its very high reactivity, which would unpredictably affect the grafting process.

TABLE 1

Solvents used to dissolve mateimides.

| Monomer Number | Solvent Used |
|---|---|
| 1 | Ethanol[a] |
| 2 | Acetone[a] |
| 3 | Ethanol[a] |
| 4 | Ethanol[a] |
| 5 | DI Water[b] |
| 6 | Ethanol[a] |
| 7 | DI Water[b] |
| 8 | Ethanol[a] |
| 9 | Ethanol[a] |

[a]Pure solvent, used as received
[b]DI water filtered through a 0.22 μm Stericup PES membrane

TABLE 2

Synthesized monomers 6 and 11.

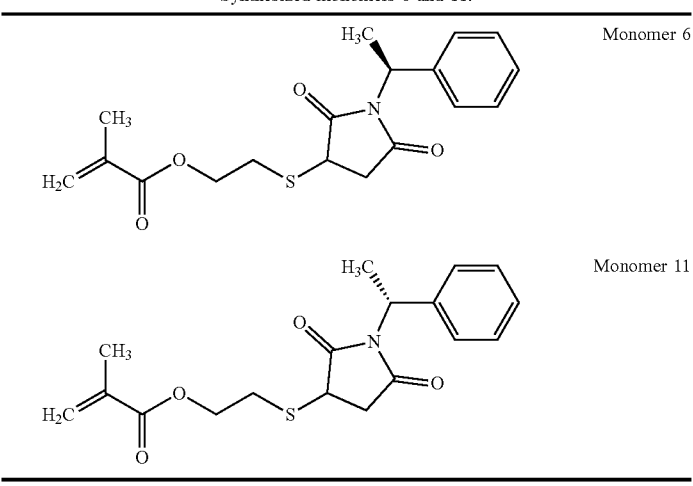

High Throughput-Atmospheric Pressure Plasma (HTP-APP)

The 96 well membrane plates were pre-soaked in DI water overnight prior to modification. They were then filtered with 200 μL pre-filtered DI water for 2 min. with a transmembrane pressure of 68 kPa (−20 in. Hg) and at room temperature. Membranes located at the base of each well in the 96 well filter plate were exposed to an atmospheric pressure plasma (APP) source (Model ATOMFLO, Surfx Technologies LLC, Culver City, Calif.) at a helium flow rate of 30.0 L min$^{-1}$, an oxygen flow rate of 0.4 L min$^{-1}$, and a source-to-membrane distance of 20 mm. The plasma source was operated at 140 V and driven by a radio frequency power at 27.12 MHz. An XYZ Robot (Surfx Technologies LLC, Culver City, Calif.) was used to control the plasma source over the plate with a scan speed of 6 mm s$^{-1}$. Following exposure to the plasma and subsequent formation of radicals at the membrane surface, 200 μL of monomer solution was added to each well in the filter plate. Graft polymerization was immediately initiated at 60±1° C. for 2 h. The reaction was terminated by adding pre-filtered DI water (filtered using a 0.22 μm PES Stericup. Millipore, Billerica, Mass.). The 96 membrane filter plate was then soaked and rinsed with DI water for 24 h to remove any homopolymer and unreacted monomer residue from the membrane surfaces. Finally, the plates were filtered twice with 200 μL of pre-filtered DI water for 2 min. through a vacuum manifold (Pall, Port Washington, N.Y.) using a transmembrane pressure (TMP) of 68 kPa (−20 in. Hg). Degree of grafting was not measured because attenuated total reflection infrared spectroscopy (ATR-FTIR) does not show high absorbance peaks at this monomer concentration. This concentration is used to study the effects of the surface chemistry alone, not the effects of three dimensional chain polymerization, which requires much higher monomer concentration (typically 1-4M, depending upon monomer used).

Assay for Protein Adhesion: High Throughput Filtration and Evaluation

After static fouling, filtration of PBS solution in a 96-well filter plate was performed on a multi-well plate vacuum manifold (Pall Corp. Port Washington, N.Y.) at a constant transmembrane pressure (TMP) of 68 kPa and T=22±1° C. The permeate was collected in an acrylic 96-well receiver plate (Corning Inc., Owning, N.Y.), placed under the 96-well filter plate, establishing well-to-well alignment. The volume of permeate in each receiver well was calculated by measuring the absorbance at 977 nm of permeate solution in the receiver plate wells using a Microplate Spectrophotometer (PowerWave XS, BioTek Instruments Inc., Winooski, Vt.) and compared with a standard curve. Permeation flux, $J_v$ (m s$^{-1}$), is defined as $J_v=V/(At)$, where V (m$^3$) is the cumulative volume of permeate, A (m$^2$) is the membrane surface area, and t (s) is the filtration time. Membrane resistance is defined as $R=\Delta P/\mu J_v$, where $\Delta P$ (Pa) is TMP and μ (kg m$^{-1}$ s$^{-1}$) is the solution viscosity. The protein adhesion and subsequent pore blocking (i.e. anti-fouling performance) was measured in terms of a fouling index, $\mathfrak{R}$:

$$\mathfrak{R} = [(R_{Fouled}-R_{PBS})_{mod}/(R_{Fouled}-R_{PBS})_{control}] \quad (1)$$

where, $\mathfrak{R}$ is defined as the ratio of the increase in resistance due to BSA fouling of the modified membrane to the control or unmodified membrane, $R_{PBS,mod}$ and $R_{PBS,control}$ are resistances to the PBS flux for the modified and unmodified membranes before BSA fouling, respectively, and $R_{Fouled,mod}$ and $R_{Fouled,control}$ are resistances to the PBS flux for the modified and unmodified membranes after BSA fouling, respectively. $\mathfrak{R}$ <1 indicates that the modified membranes exhibited less BSA fouling than the control or unmodified membrane. Membrane selectivity was measured after filtration of 1 mg/mL BSA solution in PBS for 2 min. at a TMP of 68 kPa (dynamic fouling) at room temperature and is defined as:

$$\psi = C_b/C_p \quad (2)$$

where $C_b$ and $C_p$ are the BSA concentrations in the feed (before filtration) and the permeate (after filtration), respectively. The BSA concentration in the permeate was calculated by measuring the absorbance at 280 nm of permeate solution in the receiver plate wells and compared with a standard curve.

Hansen Solubility Parameter Calculation

Figure 3:
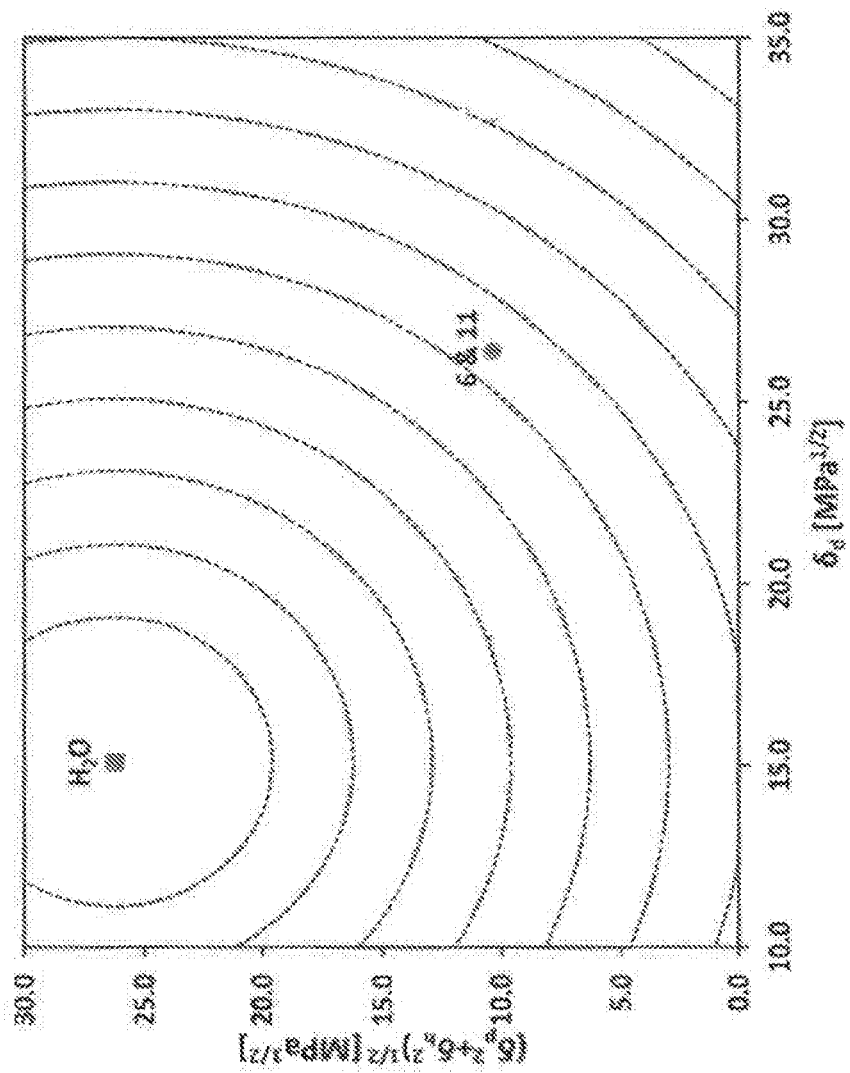
FIG. 3 depicts the Hansen solubility parameters of $(\delta_p^2 + \delta_h^2)^{1/2}$ versus $\delta_d$ of synthesized monomers 6 and 11, and water.

Hansen solubility parameters (HSPs) were calculated in an attempt to try to predict the surface properties of modified PES membrane surfaces. HSPs are defined as the square root of the cohesive energy density and used to characterize the physical properties of the modified surfaces. HSPs consist of three components (i) "non-polar" or dispersion interactions ($\delta_d$), (ii) "polar" or permanent dipole-permanent dipole interactions ($\delta_p$), and (iii) hydrogen bonding interactions ($\delta_h$). Each component is estimated from the molecular physical properties of each molecular group in a monomer. Here, a group contribution method was used:

$$\delta_d = (\Sigma F_d)/V \tag{3}$$

$$\delta_p = (\Sigma F_p^2)^{1/2}/V \tag{4}$$

$$\delta_h = (\Sigma U_h/V)^{1/2} \tag{5}$$

Where $F_d$ ($J^{1/2}$ cm$^{3/2}$ mol$^{-1}$), $F_p$ ($J^{1/2}$ cm$^{3/2}$ mol$^{-1}$), and $U_h$ (J mol$^{-1}$) are the molar attraction constants for the non-polar groups, the molar attraction constants for the polar groups, and for the hydrogen bonding energy, respectively, and V (cm$^3$ mol$^{-1}$) is the monomer molar volume. These were tabulated using the relevant tables from a Handbook of Solubility Parameters. Hansen solubility parameters are shown in FIG. 3. They are purely theoretical and not experimental and are based on the structure of each monomer. The results are plotted in relation to water since water interactions play a critical role during protein binding with surfaces in aqueous solutions.

Results and Discussion

Anti-Fouling Performance of Modified PES Membranes

Figure 2:
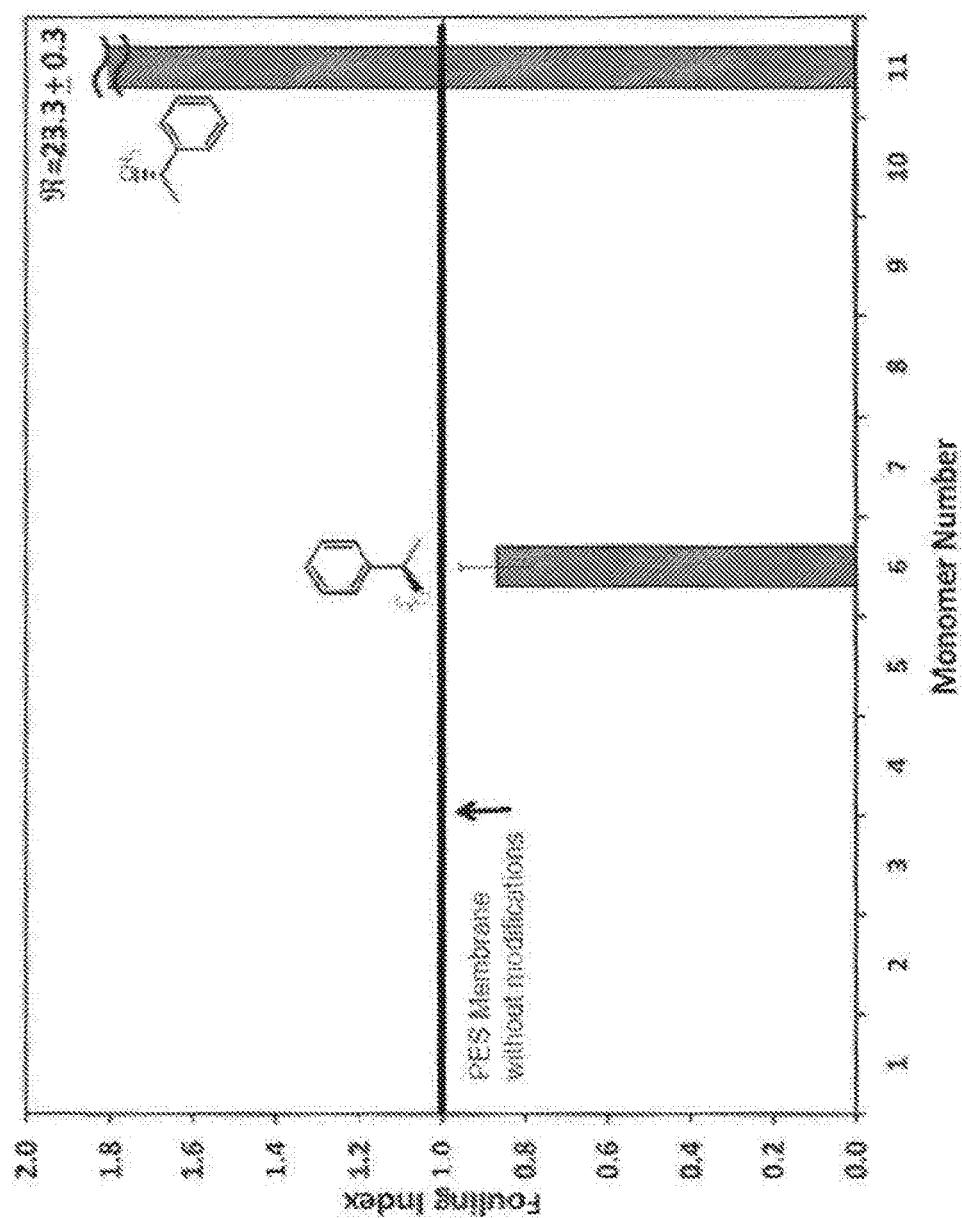
FIG. 2 provides a graph showing the fouling index ($\Re$) values versus monomer number for the synthesized monomers 6 and 11. The R groups are shown above each bar in the graph. The dotted bond connects to the nitrogen of the maleimide ring for the monomers. The performance of the PES membrane without modifications is shown as a bolded line at a fouling index of 1.0.

The filtration performance of the newly synthesized monomers, as characterized by fouling index ($\Re$) is shown in FIG. 2. The fouling index is calculated by $$\Re = [(R_{Fouled} - R_{PBS})_{mod}/(R_{Fouled} - R_{PBS})_{control}]$$

Monomer 6 had $\Re$ value lower than the unmodified control membranes (<1). Monomer 11 performed worse than the unmodified control membranes and performed substantially worse than Monomer 6. Monomer 11 had a fouling index of 23.3+0.3. Monomers 6 and 11 are chiral enantiomers, differing only by the stereochemistry of one carbon. Monomer 11 has the same stereochemistry as proteins (R), and had a much higher fouling index than monomer 6 (S). One possible explanation, to which Applicant does not wish to be held, is that the (R) enantiomer on the surface is recognized by the (R) enantiomer of the BSA in solution.

In addition to stereochemistry, water interactions appear to play an important role in protein adhesion and hence fouling. Next, an analysis of Hansen solubility parameters for different monomers is presented and correlate their differences with protein resistance of anti-fouling properties.

Hansen Solubility Parameters

Previous studies suggest that protein resistance is mainly due to surface water interactions. The intrinsic hydration capacity of different chemical groups can be calculated from tables using only the structure of a molecule. Hansen solubility parameters (HSPs) were used to quantify the type of interactions each different surface will have with the protein foulant and surrounding water molecules. Dispersion, or non-polar, ($\delta_d$), polar ($\delta_p$), and hydrogen-bonding ($\delta_h$) interactions were calculated using the group contribution method. FIG. 3 shows ($\delta_p^2 + \delta_h^2$)$^{1/2}$ plotted against $\delta_d$ for the synthesized monomers 6 and 11. The greater the distance from water, the less affinity the monomer has for water. The dashed circles are used to help guide the eye. Monomers 6 and 11 were far away from water and therefore should exhibit the highest fouling indices. These predictions were borne out by results, except for monomer 6. A possible explanation is that monomer 6 may repulse proteins of opposite stereochemistry, while monomer 11 attracts them and fouls extensively as a result.

Development of Anti-Fouling Membranes

Anti-fouling Membranes require both a low fouling index and high permeability (low resistance to flow). The fouling index is calculated by $\Re = [(R_{Fouled} - R_{PBS})_{mod}/(R_{Fouled} - R_{PBS})_{control}]$. Static fouling was conducted with 1 mg/ml BSA in PBS at room temperature for 24 hr., pH 7.4. and a TMP of 68 kPa. First, 200 μL, of 1 mg/ml bovine serum albumin (BSA) in phosphate buttered saline (PBS) was added to each well in the 96 well membrane plate (containing both modified and unmodified (control) membranes). The plate was then covered and left to foul for 24 hrs. at pH 7.4 and room temperature. After static fouling, the protein solutions were removed and 200 μL of pure PBS was filtered through the entire plate for 2 min. at a transmembrane pressure (TMP) of 68 kPa. The permeate was collected and UV absorbance at 977 nm was read for each well. UV absorbance at 977 nm was used with a calibration curve to determine the permeate volume. This permeate volume was used to calculate resistance. Resistance is used to calculate the fouling index. All measurements were taken in triplicate and error bars represent one standard deviation.

Figure 4:
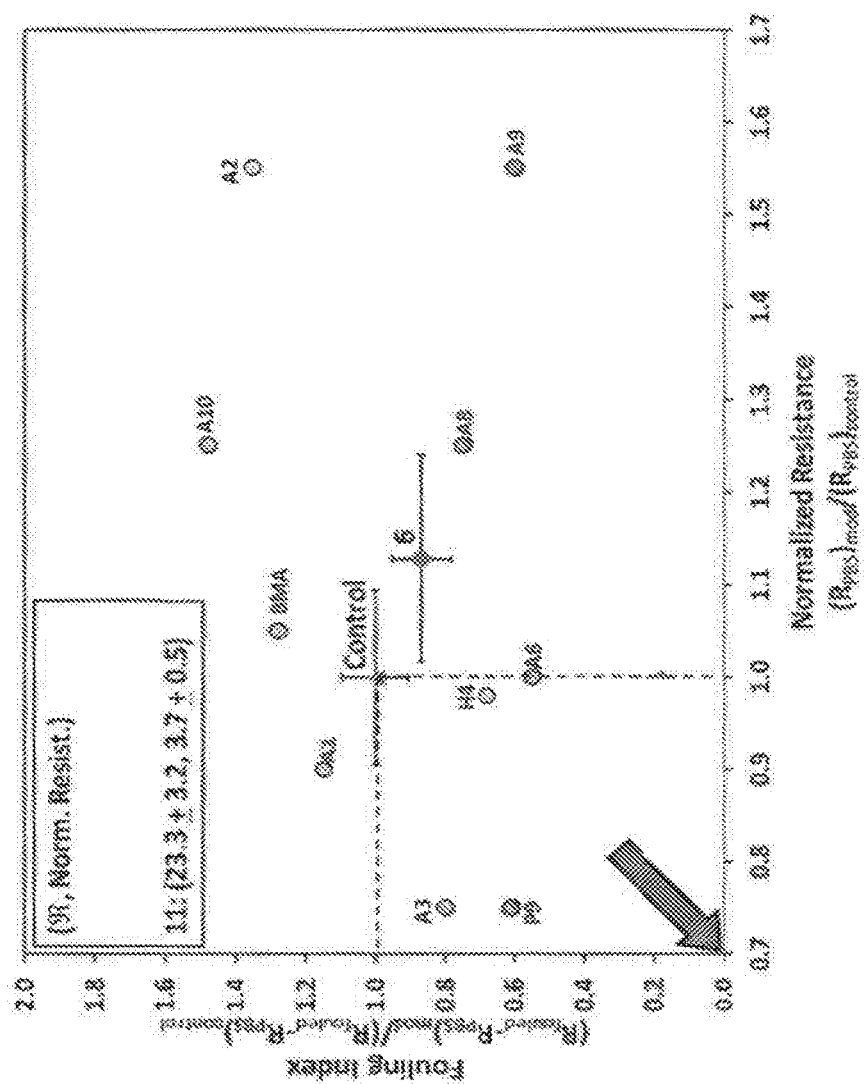
FIG. 4 depicts performance after a static fouling test, normalized by the performance for the unmodified PES membrane ($\Re_{PES,control}=1.0\pm0.1$ and $R_{PES,control}=1.0\pm0.1$).

In FIG. 4, the fouling index is plotted against the normalized resistance, which is the ratio of resistance to flow of the modified membrane to the unmodified control membrane. Normalized resistance is a measure of additional resistance imparted to the membrane from the surface chemistry modification alone. Data for previously synthesized amide monomers (A1-A3, A6, and A8-A10) as well as three previously tested commercial monomers (PEG #9 (P9), Hydroxyl #4 (H4), butyl methacrylate (BMA)) are given for reference from earlier work. Membrane modified with monomer 6 exhibited lower fouling index than the control membrane (FIG. 2). Monomer 6 had much higher resistance than the control membrane. Monomer 11 performed poorly, with a fouling index of 23.3±3.2 and normalized resistance of 3.7+.0.5. Monomer 11 is the other enantiomer of monomer 6 and likely fouled extensively since it has the same (R) stereochemistry as proteins.

Dynamic Fouling (Selectivity vs. Permeability)

In addition to anti-fouling properties, we also want to achieve high selectivity and high permeability. Previously, others have plotted separation factor vs. permeability and found that there was an upper bound above which no membrane separations could achieve.

Dynamic fouling was conducted with 1 mg/ml BSA in PBS at room temperature, pH 7.4, and a TMP of 68 kPa for 2 min. First, 200 μL of 1 mg/ml bovine serum albumin (BSA) in phosphate buffered saline (PBS) was added to each well in the 96 well membrane plate (containing both modified and unmodified (control) membranes) as in static fouling. The plate was then immediately filtered for 2 min. at a transmembrane pressure (TMP) of 68 kPa. The permeate was collected and UV absorbance at 280 nm was read for each well. UV absorbance at 280 nm was used with a calibration curve to determine the protein concentration. This was used with the initial protein concentration (1 mg/ml) to calculate selectivity. All measurements were measured in triplicate and error bars represent one standard deviation.

Figure 5:
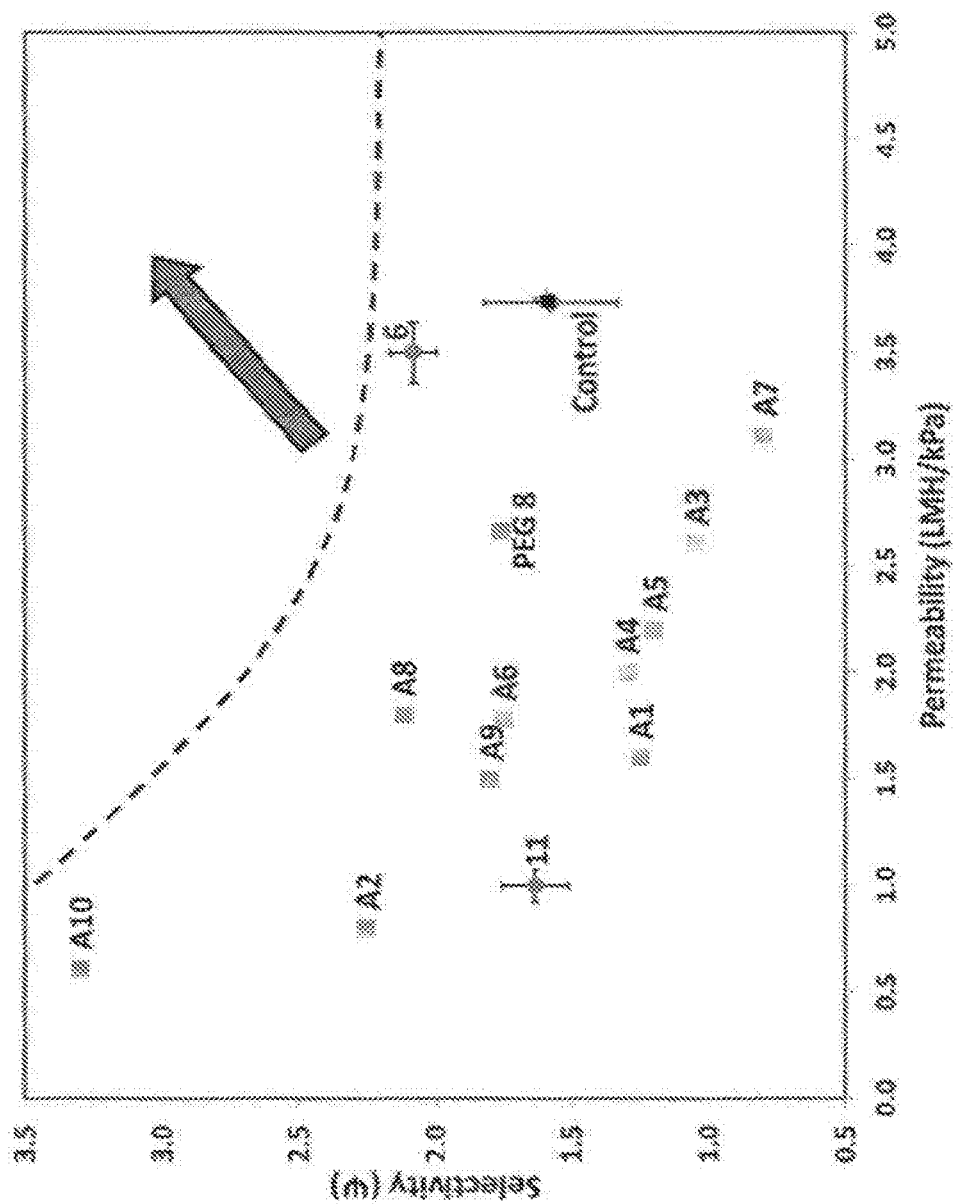
FIG. 5 depicts performance after dynamic fouling test.

Here, selectivity is plotted against permeability (FIG. 5). Selectivity is measured as the ratio of the permeability of the small molecules in PBS to that of the less permeable BSA and is plotted against permeability. The classic trend can be seen, in that membranes with high selectivity have low permeability and vice versa. The dotted line is drawn for reference and is not a fitted parameter. Most of the previously synthesized amide monomers had lower permeability than the control but some had slightly higher selectivity. Monomer 11 had a lowest permeability (1.0 LMH/kPa), as predicted. Monomer 6 had higher selectivity, but lower permeability than the control. This can also be attributed to the chirality of monomer 6. It does not stack well with proteins, therefore it retains them while still maintaining a high flux. These data support our hypothesis that water interactions play a major role in protein filtration processes.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

What is claimed is:

1. A method of modifying a surface, the method comprising:
    applying sufficient energy to a surface to induce covalent bonding with an optically active monomer; and
    contacting the optically active monomer with the surface wherein the optically active monomer is a compound of the following Formula I:

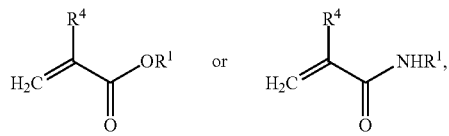

[Formula I]

wherein $R^1$ is a maleimide derivative in which $R^1$ contains at least one chiral center, and $R^4$ is H or $CH_3$.

2. The method of modifying a surface according to claim 1, further comprising
    contacting an initiating agent with the surface onto which the optically active monomer is to be covalently bound.

3. The method of modifying a surface according to claim 1, the method comprising:
    providing a poly(aryl sulfone) membrane having a surface;
    exposing the surface of the poly(aryl sulfone) membrane to an atmospheric pressure plasma (APP) source;
    contacting an optically active monomer with the exposed surface of the poly(aryl sulfone) membrane; and
    applying heat to the surface of the poly(aryl sulfone) membrane.

4. The method of modifying a surface according to claim 3, further comprising:
    contacting an initiating agent with the surface of the poly(aryl sulfone) membrane.

5. The method of modifying a surface according to claim 3, further comprising:
    contacting the heated surface of the poly(aryl sulfone) membrane with water.

6. The method of claim 3, wherein the APP source is helium and oxygen gases.

7. The method of claim 3, wherein the optically active monomer is a compound of the following Formula II:

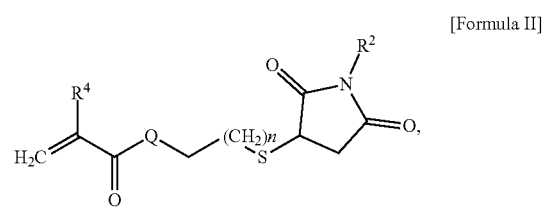

[Formula II]

wherein R2 is an optically active substituent,
n is a number from 1 to 6,
Q is NH or O, and
$R^4$ is H or $CH_3$.

8. The method of claim 7, wherein $R^2$ is

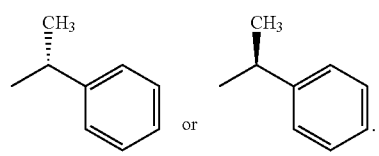

9. The method of claim 7, wherein the optically active monomer is a compound of the following Formula III:

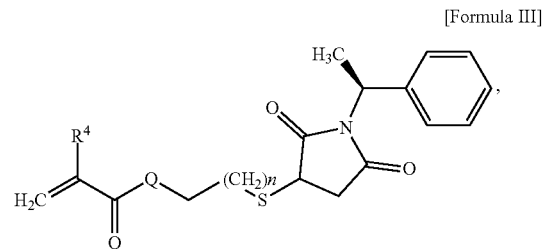

[Formula III]

wherein Q is NH or 0,
n is a number from 1 to 6, and
$R^4$ is H or $CH_3$.

10. The method of claim 7, wherein the optically active monomer is a compound of the following Formula IV:

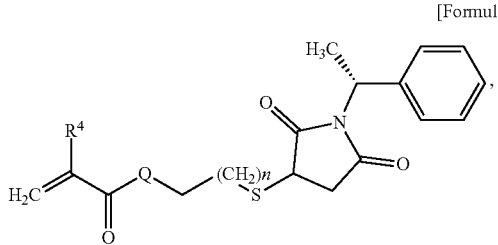

[Formula IV]

wherein Q is NH or O,
n is a number from 1 to 6, and
$R^4$ is H or $CH_3$.

11. The method of claim 3, wherein the poly(aryl sulfone) membrane is exposed to heat in the range from 30° C. to 100° C.

12. The method of claim 11, wherein the poly(aryl sulfone) membrane is exposed to heat in the range from 50° C. to 70° C.

13. The method of claim 3, wherein the poly(aryl sulfone) membrane is exposed to heat for 1 to 4 hours.

14. The method of claim 3, wherein the heat is applied by placing the poly(aryl sulfone) membrane in an oven at a temperature between 50 to 70° C. for 1 to 4 hours.

15. A method of synthesizing an optically active monomer comprising:
providing a solution comprising bis(2-methacryloyl)oxyethyl disulfide, wherein the bis(2-methacryloyl)oxyethyl disulfide has been contacted with a tris(2-carboxyethyl)phosphine (TCEP) reducing gel;
providing a solution comprising an optically active maleimide;
mixing the disulfide and maleimide solutions;
centrifuging the mixed solution; and
removing the TCEP reducing gel.

16. The method of claim 15, wherein the optically active maleimide is (R)-(+)-N-(1-Phenylethyl)maleimide.

17. The method of claim 15, wherein the optically active maleimide is (S)-(−)-N-(1-Phenylethyl)maleimide.

18. The method of claim 15, wherein the solution comprising an optically active maleimide is miscible with water.

19. The method of claim 15, the method further comprising:
rotating the mixed solution for 12 to 28 hours at a temperature between 20° C. to 25° C.

* * * * *